US009828157B2

(12) United States Patent
Roesler

(10) Patent No.: US 9,828,157 B2
(45) Date of Patent: Nov. 28, 2017

(54) METHODS OF PACKAGING AND PACKAGING FOR SHARP-EDGED TOOLS

(71) Applicant: Peter Roesler, Wangen (DE)

(72) Inventor: Peter Roesler, Wangen (DE)

(73) Assignee: Rose Plastic AG (DE)

( * ) Notice: Subject to any disclaimer, the term of this patent is extended or adjusted under 35 U.S.C. 154(b) by 0 days.

(21) Appl. No.: 14/202,325

(22) Filed: Mar. 10, 2014

(65) Prior Publication Data
US 2014/0251845 A1    Sep. 11, 2014

(30) Foreign Application Priority Data

Mar. 9, 2013    (DE) ......................... 10 2013 004 168

(51) Int. Cl.
| *B65D 83/10* | (2006.01) |
| *B65D 77/02* | (2006.01) |
| *A61B 50/30* | (2016.01) |
| *A61B 50/33* | (2016.01) |
| *A61B 50/00* | (2016.01) |
| *A61B 17/14* | (2006.01) |

(52) U.S. Cl.
CPC .............. *B65D 77/02* (2013.01); *A61B 50/30* (2016.02); *A61B 50/3001* (2016.02); *A61B 50/33* (2016.02); *A61B 17/142* (2016.11); *A61B 2050/0065* (2016.02)

(58) Field of Classification Search
CPC .............. A61B 19/026; A61B 19/0262; A61B 19/0271; A61B 19/0231; A61B 19/0256; A61B 17/14; A61B 2019/0219; A61B 12/3215; B65B 67/08; B65D 77/02; A61L 2/26

USPC ........... 220/363; 606/178; 53/461; 206/317, 206/361, 806, 597, 779, 471, 379; 30/360, 152, 286

See application file for complete search history.

(56) References Cited

U.S. PATENT DOCUMENTS

| 3,123,211 | A |   | 3/1964  | Sorensen |
| 3,533,503 | A | * | 10/1970 | Keats et al. .................. 206/776 |
| 3,669,256 | A |   | 6/1972  | Jacob |
| 4,736,842 | A | * | 4/1988  | Uetake et al. ................ 206/363 |
| 5,727,682 | A |   | 3/1998  | Abidin et al. |
| 6,161,695 | A |   | 12/2000 | Nicolais |
| 7,024,773 | B2| * | 4/2006  | Jennings ................. B26B 29/02 30/151 |
| 7,316,318 | B1|   | 1/2008  | Rosten et al. |
| 8,083,058 | B2| * | 12/2011 | Marcinkowski ....... B65D 77/26 206/352 |

(Continued)

FOREIGN PATENT DOCUMENTS

| DE | 19725499 A1    | 12/1998 |
| DE | 202007019275 U1 | 1/2012  |

*Primary Examiner* — Anthony Stashick
*Assistant Examiner* — James M Van Buskirk
(74) *Attorney, Agent, or Firm* — Cohen & Grigsby, PC

(57) ABSTRACT

Packaging and methods for packaging tools having a sharp or cutting edge, such as surgical tools, in which the tool is packaged under sterile conditions. The tool may be packaged first—at least partially—and in particular with its sensitive cutting edges and working surfaces packaged in a protective package. The protective package containing at least the cutting or working surfaces of the tool may then be secured in a fixed position in an outer blister pack, which may be sealed with a sealing film.

6 Claims, 3 Drawing Sheets

(56) References Cited

U.S. PATENT DOCUMENTS

| | | | |
|---|---|---|---|
| 8,303,599 B2* | 11/2012 | Hess et al. ...................... | 606/92 |
| 2004/0124105 A1* | 7/2004 | Seiler ................ | A61M 37/0069 |
| | | | 206/363 |
| 2011/0036736 A1* | 2/2011 | Knowlton ............ | A61B 19/026 |
| | | | 206/438 |

* cited by examiner

METHODS OF PACKAGING AND PACKAGING FOR SHARP-EDGED TOOLS

BACKGROUND

1. Technical Field of the Invention

This invention pertains generally to sterile plastic packaging for the storage of items having a cutting or sawing edge. More specifically, the invention includes a two-part package comprising a first protective package which holds the item and a second blister pack which holds the first package in a fixed position therein.

2. Description of the Related Art

The presently disclosed invention is described in connection with a surgical instrument such as an oscillating saw or a bone saw or the like is assumed as an example of a surgical instrument. The description of an oscillating saw with a sharp-edged serrated blade is thus to be understood only as an example without limiting the scope of the invention.

In packaging sterile surgical tools, it is known that these surgical tools may be packaged in a polybag. The disadvantage of this type of packaging is that the sterile surgical tool, which may have sensitive cutting or sawing edges, can slip around unprotected in the interior of the polybag during shipping and handling of the package and may thus come in contact with the inside surfaces of the polybag. Microfine particles from the plastic packaging can therefore enter the blade area of the surgical tool in an unwanted manner. There is thus the risk during surgery that these particles—possibly invisible—may be introduced into the surgical wound, which could result in serious tissue irritation in the surgical area.

In the past, there has not been an acknowledged method of sterile packaging of surgical tools in such a way that the package cannot be damaged even if it falls on the ground during shipping and handling. The object of the present invention is therefore to provide a package for, and a method for, packaging tools having a sharp or cutting edge such as, for example, surgical tools. The package and method of use thereof will make it possible to store tools having a sharp edge under sterile conditions so that they are free of contamination and damage, and ensures that the tools can be removed from the package in a sterile and undamaged condition when the package is opened.

SUMMARY

The presently disclosed invention overcomes many of the shortcomings of the prior art by providing a two-part package, and method of use of such, which maintains a tool having a sharp or cutting edge securely within a first package which is then held securely within a second blister-pack package. In accordance with the disclosed invention, a tool is first packaged—at least partially—and in particular with its sensitive cutting edges and working surfaces in a (first) protective package and this protective package together with the surgical tool packaged therein is placed in a (second) blister pack, where it is held in a secure position and sealed with a sealing film after the position has been secured.

This technical teaching yields the advantage of a two-step type of packaging which provides that the surgical tool with its sensitive blades and working edges is packaged in a first protective package, so that the sensitive parts of the surgical tool cannot come in contact with any plastic parts of the protective package. For this reason, a protective package is provided in the first step, its volume being designed so that the parts of the surgical tool that are sensitive to contact are held in a non-contact accommodation in the interior of the protective package. There is therefore no risk that the sensitive parts will come in contact with the plastic surfaces on the inside of the protective package and pick up microparticles in an undesirable manner. Such a protective package is designed so that the sensitive blades or working surfaces of the surgical tool cannot come in contact with the inside surfaces of the protective package even if the protective package drops to the ground.

In a second step, it is provided that the surgical tool packaged in the protective package in this way is then placed in a blister pack and secured there in a fixed position. Due to the method of securing the tool in a fixed position in the blister pack, the surgical tool, which has already been packaged in the protective package, cannot slide back and forth in the blister pack. This could also result in microparticles being picked up in an undesirable manner. Securing the position of the protective package in the blister pack ensures that the surgical tool packaged in the protective package cannot come in contact with the walls of the blister pack along any of its surfaces to pick up unwanted microparticles there.

This double packaging (protective package and blister pack) yields the additional advantage that even with improper or careless handling and shipping, there is no risk that the sensitive blades of the surgical tool might puncture the protective package or even break out of the blister pack because double packaging is provided.

In a preferred embodiment of the invention it is provided that the fixed positioning of the surgical tool packaged in the protective package is provided only with respect to the protective package itself. This avoids any contaminating contact between the parts of the surgical tool which protrude out of the protective package and the blister pack. The unpackaged parts of the surgical tool protruding out of the protective package therefore do not come in contact with the surfaces of the blister pack.

The packaging of the presently disclosed invention therefore provides a free-standing method for holding surgical tools in an inner protective package because only the protective package itself is secured in the outer blister pack and all the other parts of the surgical tool are free-standing in the blister pack and do not come in contact with the blister pack.

The presently disclosed invention is not limited to accommodating a single surgical tool within a protective package in such a blister pack or to accommodating a single type of surgical tool in a protective package within a blister pack. That is, in certain embodiments various surgical tools may be packaged in the manner described herein, where each surgical tool is packaged in its own protective package and all the protective packages are secured in a fixed position in a blister pack. In this way, an entire set of the same or different surgical tools for a certain operation can be made available using a single blister pack. Thus, for example, two or three different saws, which are needed for a certain operation, may be accommodated in a single blister pack, with each surgical tool being packaged in its own protective package and all the protective packages being fixed in a secured position in the blister pack.

The presently disclosed invention provides that only the sensitive (front) parts of the surgical tool may be enclosed by a protective package, and the other parts—for example, the shaft parts which are provided for connecting to a machine—remain unpackaged. This reduces costs because only a partial packaging is provided as the inner protective package for the surgical tool. To prevent the parts of the surgical tool that are not covered by the inner protective package from being contaminated by coming in contact with the inside surfaces of the outer blister pack, the invention provides that the outer blister pack holds only the protective package in a fixed position but not the unpackaged parts of the surgical tool. These unpackaged parts should therefore not come into contact with the walls of the outer blister pack.

In a preferred embodiment, it is provided that the interior of the blister pack is either embodied as an air space or is filled with a protective gas. After placing the surgical tools held in the protective packages in the blister pack, the blister pack is either filled with a protective gas or remains filled with air and is then sealed at its top with a sealing film. This sealing film preferably consists of a sealable, airtight plastic material. Such sealing films have an adhesive coating, which leads to a complete and airtight seal of the interior of the blister pack after a suitable application of heat.

The term "blister pack", as used in the present patent application, is otherwise to be understood broadly. In a first embodiment of the invention, it is provided that the bottom part of the blister pack establishes a form-fitting receptacle to receive the protective package of the surgical tool. In this case, the top side of the blister pack may be provided with a smooth peripheral edge, which can be sealed with the sealing film.

In another embodiment, it is provided that the blister pack is designed in two parts and consists of a top part, which has certain receptacles for form-fitting accommodation of parts of the protective package. The top part can be connected to the bottom part which likewise has receptacles for parts of the protective package. In this case, two molded parts (top part and bottom part) can be connected to one another in a connection area by sealing, adhesive bonding, welding or the like, for example.

Such a blister pack preferably consists of a deep-drawable, gamma-radiatable plastic material. Likewise, this plastic material may be beta-radiatable, wherein both beta and gamma radiation may be used for sterilization, for example. The difference in the types of radiation lies in their ability to penetrate the material and in their dosing rate. To produce a sterile interior atmosphere inside the blister pack, it is provided that after complete airtight closure of the blister pack with the help of the sealing film or with the help of the attached to part at any subsequent point in time, sterility may be established by the fact that the blister pack is brought within the range of a beta- or gamma-radiation source. The inside of the blister pack and thus also the inside of the protective package which holds the surgical tool are sterilized.

In comparison with the prior art, the invention has the advantage that the sensitive parts of the surgical tool are surrounded completely by the protective package and held at a distance (without contact) from the inside surfaces of the protective package, so that the sealing film or the top part is removed first when the blister pack is opened. The blister pack is opened under sterile conditions in the operating room. After opening the blister pack, the protective package with the surgical tool packaged therein can be removed from the blister pack by tearing open the sealing film.

To this end, the invention provides that removal openings suitable for fingers are provided in the blister pack precisely on the side of the blister pack where the protective package is held. This ensures that the surgical tool packaged in the protective package may only be removed from the blister pack by gripping the protective package.

This is an advantage over the prior art where it was known only that the surgical tool is accommodated in the region of the shaft in a fixed position in a package. This had the disadvantage that when opening the package the surgeon would grip the tool precisely on the end opposite the shaft, namely on the sharp, sensitive blade, which must be protected from contamination, and thus the surgeon might contaminate the blade or injure his glove to such an extent that particles would come in contact with the blade. This can in turn lead to serious surgical complications. There was also the risk that by gripping the cutting edges of the surgical tools while wearing gloves, the gloves might be damaged and the blade might come in contact with the surgeon's skin, which would thus compromise sterility in the operating field.

The presently disclosed invention further provides that the removal openings in the blister pack may be placed in the area of the protective package and that the protective package surrounds precisely the surgical blades and working surfaces of the surgical tool that are to be protected, holding them at a distance so that there is no contact with package surfaces.

This provides the advantage that the surgical tool is grasped by holding the protective package at the level of the packaged blade, so the surgeon can immediately insert the shaft, which is protruding out of the protective package into the respective machine. The machine may have a coupling fitting, for example, for the shaft of the surgical tool to couple with. The protective package may then be removed only after successful coupling of the shaft of the surgical tool. The machine can then be held in one's hand and the protective package subsequently removed. There is no danger that the surgeon's gloved hand might come into the region of the blade of the surgical tool because the opening in the protective package is from the rear (shaft end) of the surgical tool and not from the front, from the cutting end.

The protective package is therefore removed from the shaft end just before the surgery, i.e., with the machine being held securely and with the surgical tool coupled, so there is no risk that the surgeon's gloved hand might enter the working or cutting range of the surgical tool.

Another advantage of the invention is that the protective package need not be adapted to the shape of the surgical tool. The protective package is designed so that a plurality of different shapes of surgical tools, for example, bone saws, scalpels, cutting tools and the like can be accommodated with a gripping effect in a standardized protective package, where the common feature of this holder is that the sensitive cutting and working surfaces of the surgical tool accommodated in the protective package are held so that there is no contact with the inside wall of the protective package. The volume of the protective package is selected to be so large in comparison with the packaged volume of the surgical tool that the packaged parts cannot come in contact with the inside surfaces of the protective package even in free fall of the protective package to the ground.

In a preferred embodiment, different surgical tools are therefore each held with a gripping effect in the protective package, eliminating the need for a form-fitting holder that would have to be adapted to the particular shape of the tool. That is, in a holder with a gripping effect, a variety of different surgical tools can be held in the protective package, regardless of their precise shape.

There is thus the advantage that only the protective package need be adapted to the blister pack according to the invention in a secured position, so it is suitable for holding a plurality of different surgical tools because a standard blister pack based only on the type of protective package to be held may be used here but not based on the type of surgical tool to be secured. This results in a universal usability of the blister pack according to the invention.

Thus a fully automatic packaging of large quantities of surgical tools in blister packs becomes possible for the first time because the blister pack must always be based only on securing the position of a universal protective package but not on different surgical tools.

All the information and features disclosed in these documents, including the abstract, in particular the three-dimensional formation depicted in the drawings, make up the presently disclosed invention, inasmuch as they are novel individually or in combination in comparison with the prior art.

BRIEF DESCRIPTION OF THE DRAWINGS

The invention is explained in greater detail below, illustrating only one type of embodiment. Additional features that are essential to the invention and advantages of the invention are derived from the drawings shown herein, which include.

DETAILED DESCRIPTION

Figure 1:
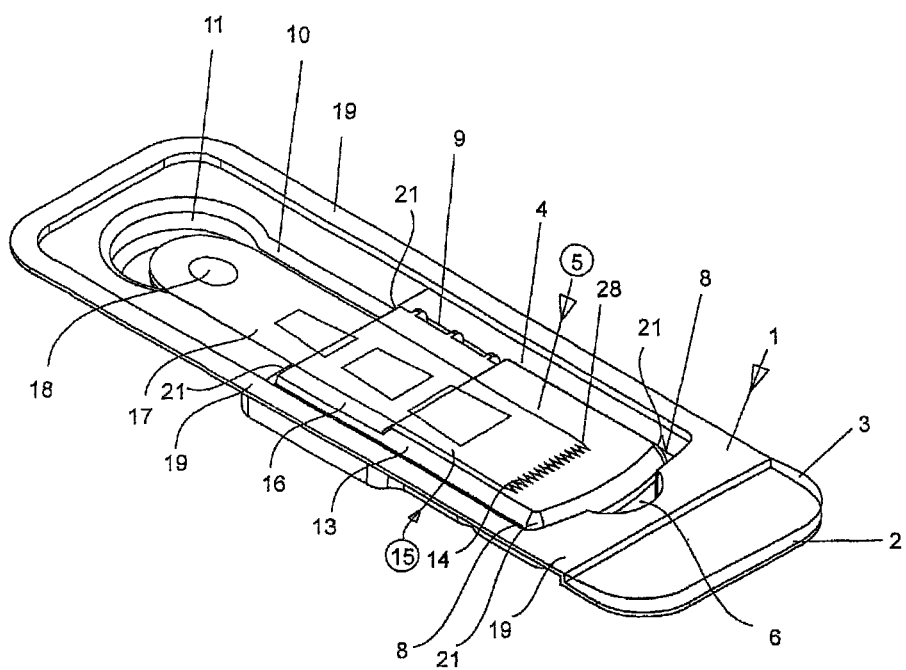
FIG. 1 illustrates a schematic view from above of an opened blister pack containing a protective package with a surgical tool packaged therein.
Figures 2, 3:
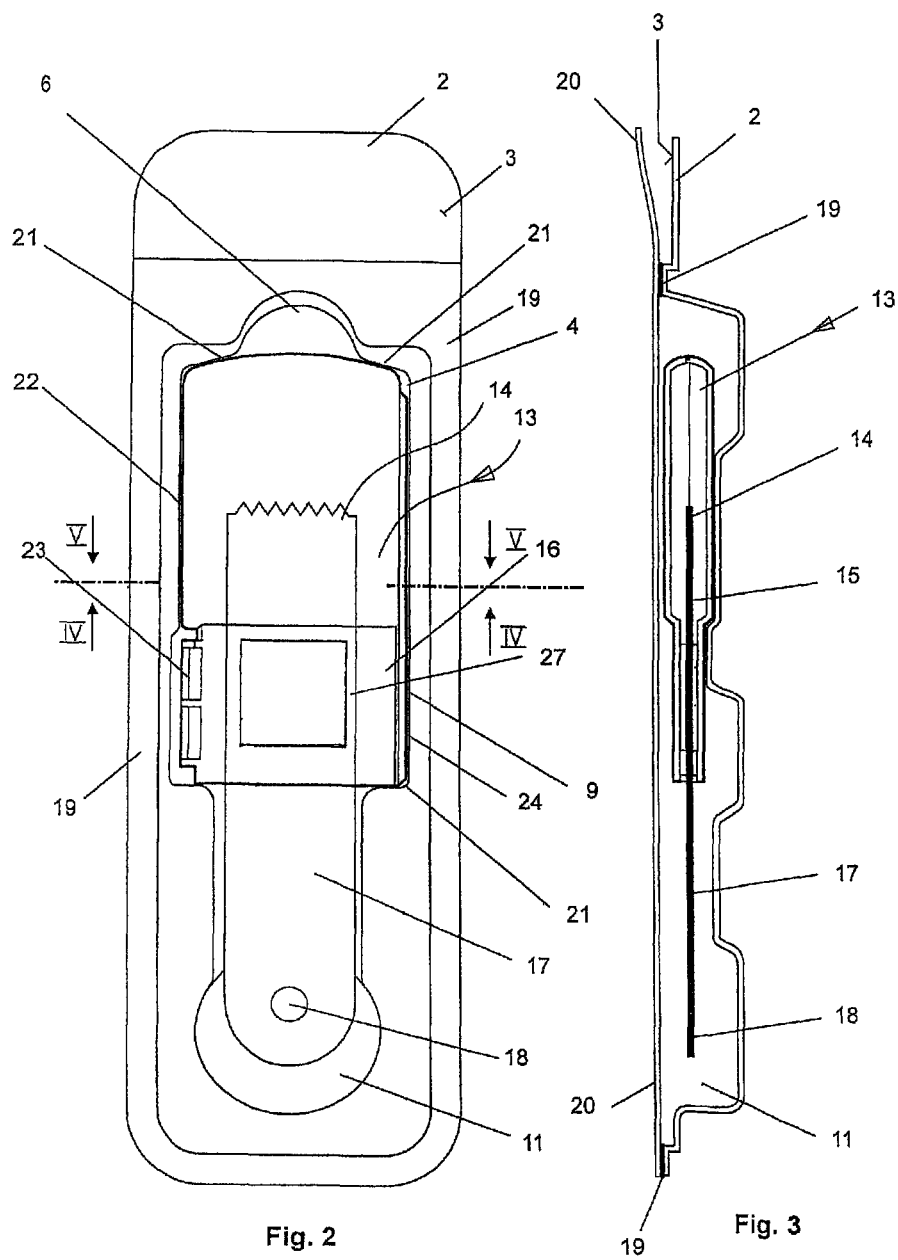
FIG. 2 illustrates a top view of the arrangement from FIG. 1.
FIG. 3 illustrates the section through the arrangement according to FIG. 1 and FIG. 2.

Referring now to the drawings, FIGS. 1-7 illustrate embodiments of the packaging system of the presently disclosed invention. The figures illustrate in general a bottom shell 1 of a blister pack made of a deep-drawable plastic material. A safety container or protective container 13 may be inserted into the bottom shell in a secured position which is inserted into the interior 29 of bottom dish 1 of the blister pack.

In the exemplary embodiment shown here, stop surfaces 21, which cooperate with the respective stop surfaces on the outside wall of the protective container 13 are provided in the interior 29 of the bottom shell 1 of the blister pack, so that the protective container 13 is held in a fixed position in the bottom shell 1 without tilting or twisting.

The protective container 13 in turn accommodates the surgical tool 15 to be protected, wherein the sensitive blade 14 of the tool 15 is accommodated in the protective container 13 at a distance from all the inside surfaces of the protective container 13 in a non-contact accommodation. This ensures that the blade 14 of the tool 15 will not come in contact with a plastic surface of the protective container 13.

The tool shaft 17 of the tool 15 protrudes out of the rear side of the protective container 13 and protrudes with play and while maintaining a distance (without contact) into the interior of the bottom shell 1. Consequently, only the protective container 13 may be held in a secure position and the tool shaft 17 protruding out of the protective container 13 may be supported in a smaller assigned receiving opening 10 in the bottom shell 1, while retaining a contact distance. The rear part of the tool shaft 17 may be held in a round receptacle opening 11 while retaining a contact distance.

This ensures that the tool shaft 17 of the tool 15 accommodated in the protective container 13 will not come in contact with the material of the bottom shell 1 of the blister pack at any point and be unintentionally contaminated there. This is thus a free-standing support of the surgical tool, as is also apparent from FIG. 6.

The bottom shell 1 has a top peripheral sealing face 19 and forms a pull strip 2 directed toward the front. The pull strip 2 may be connected to the remaining material of the bottom shell 1 as one piece of material. The sealing film 20 lies loosely over the pull strip 2 and can be pulled away there. It rests on the surrounding sealing face 19 and may be sealed there in an airtight manner.

The surface 3 of the pull strip 2 sits below the plane of the sealing face 19, so that the sealing film 20 can be gripped easily by hand in this area and pulled upward.

The protective container 13 may be held in the larger receptacle opening 4 in the area of the interior 29 of the bottom shell 1 in a fixed position. The protective container has counter faces 22, which cooperate with the respective stop faces 21 in the bottom shell 1, to thereby hold the protective container 13 in the receptacle opening 4 of the bottom shell 1, so that it is fixed in position and is free of tilting and twisting.

This ensures that the protective container 13 can be removed from the bottom shell 1 when the sealing film 20 is torn off. A handle opening 6 in the bottom shell 1, which may be arranged in the area of the pull strip 2 and maintains the distance at the end face, can be used for removal of the protective container 13 from the bottom shell 1.

Figure 7:
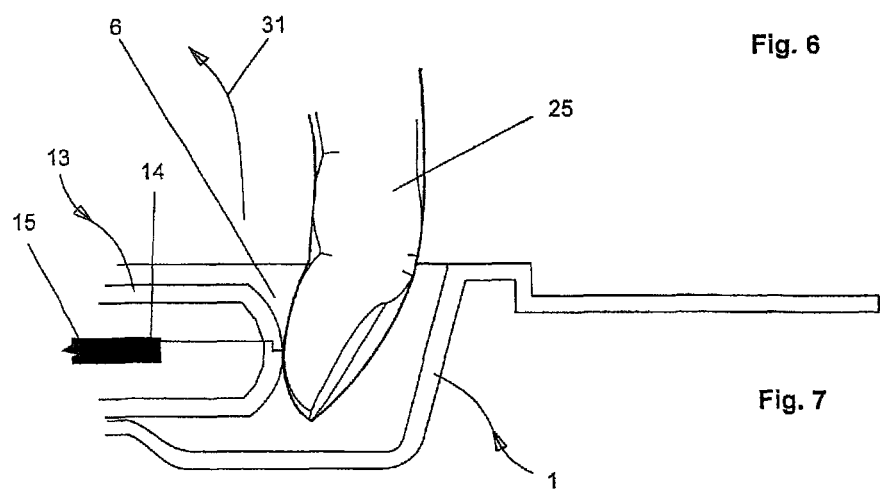
FIG. 7 illustrates the detail from FIG. 6 illustrating the engagement opening for removing the protective package.

According to FIG. 7, the protective container 13 is removed in the direction of the arrow 31 by gripping with the finger 25 on one hand into the handle. The hand thus holds the protective container 13 securely and the sensitive blade 14 of the tool 15 is still held free-standing and in a secured position in the protective container 13. In this situation, the protective container 13 is gripped and the tool shaft 17 is supplied to a tool (not shown in detail here) with its coupling receptacle 18, which establishes a coupling with the tool shaft 17.

The protective container 13 may be removed only when the tool 15 has been coupled by the tool shaft 17 to the machine while still packaged. This is done in a sterile atmosphere because the sealing film 20 is removed from the blister pack according to the invention only in the sterile operating room.

Figure 4:
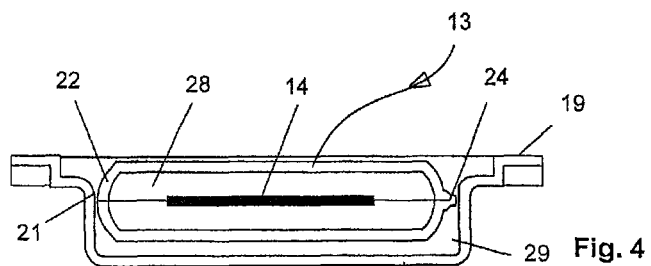
FIG. 4 illustrates the section through the arrangement according to FIG. 2 as seen in the direction of the arrow IV-IV.
Figure 5:
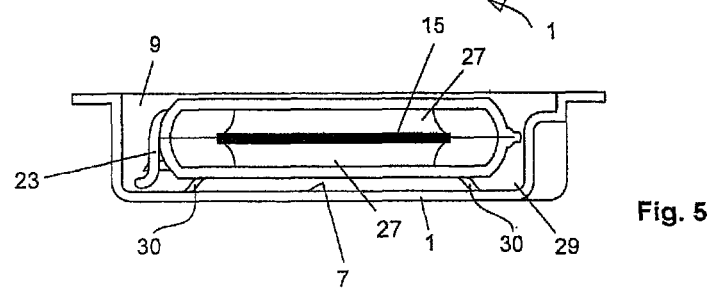
FIG. 5 illustrates the section through the arrangement according to FIG. 2 as seen in the direction of the arrow V-V.
Figure 6:
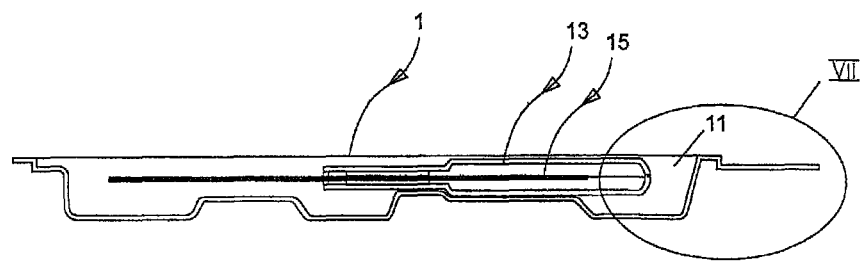
FIG. 6 illustrates the same diagram as that in FIG. 3 except that it shows a detail according to FIG. 7.

FIGS. 4 and 5 show that the bottom side of the protective container 13 is a distance away from the bottom 7 of the bottom shell 1, and there are spacer ribs 30, which maintain the protective container 13 with respect to the bottom of the bottom shell 1.

FIG. 1 shows that the side edges 8 in the area of the protective container 13 form the stop faces for the holder in the area of the larger receptacle opening 4.

The closure 23 of the protective container 13 established by catch means is held in a clearance, namely in a receptacle opening 9, to also prevent the closure 23 from coming in contact with the container surfaces of the bottom shell 1.

A folding hinge 24, preferably embodied as a film hinge, is integrally molded on the side of protective container 13 opposite the closure 23.

The tool 15 to be protected is held in the protective container 13 by the fact that the tool shaft 17 is enclosed with a gripping effect between the top and bottom sides by two elastomeric holding elements 27. This is illustrated in a sectional view in FIG. 5.

However, the end of the tool shaft 17 pointing in the direction of the front end (blade 14) is free of any contact with surfaces of the blister pack, so that the blade 14 protrudes completely freely into the interior of the protective container 13 without any contact, as shown in FIG. 4. Thus the interior 28 of the protective container 13 is held without contact with the blade 14.

FIG. 5 shows that the protective container 13 can be carried and supported in its rear part by molded ribs 30 on the bottom 7 of the bottom shell 1. This shaping of the bottom shell is designed with a receptacle opening 4, so that the receptacle opening 4 surrounds the protective container 13 at least partially in a form-fitting manner, so that only the protective container 13 is accommodated in a fixed position in the bottom shell 1, but the tool 15 accommodated in the protective container 13 does not come in contact with any surface of the bottom shell 1.

This creates a blister pack which is opened only in the sterile operating room, where the protective container 13 is gripped with a finger 25, while the sensitive blade 14 is protected from contact and the tool 15, which is still packaged in the protective container, is inserted into a machine and coupled there. Only then is the protective container 13 removed just before the tool 15 is used for an operation.

LEGEND TO THE DRAWINGS

1 Bottom shell
2 Pull strip
3 Surface (of 3)
4 Receptacle opening (large)
5
6 Gripping opening
7 Bottom
8 Side edge
9 Receptacle opening (small)
10 Receptacle opening (small)
11 Receptacle opening (round)
12
13 Protective container
14 Blade
15 Tool
16 Holding part
17 Tool shaft
18 Coupling receptacle
19 Sealing face
20 Sealing film
21 Stop face
22 Counter face
23 Closure
24 Folding hinge
25 Finger
26
27 Holding element
28 Interior (of 13)
29 Interior (of 1)
30 Molded rib
31 Direction of arrow

What is claimed is:

1. A method of packaging sterile surgical tools, the method comprising:

placing at least the cutting edges of a surgical tool in a first protective package with internal surfaces that define an interior chamber that completely surrounds said cutting edges of said surgical tool with said cutting edges being spaced apart from all internal surfaces of said first protective package, said first protective package having a first package part that defines said interior chamber into which the cutting edges of the surgical tool protrude without contacting the internal surfaces of the first protective package, said first protective package also having a second package part that accommodates at least a portion of a shaft of the surgical tool, said second package part including at least one holding element that is configured to secure the shaft of the surgical tool in a fixed position;

placing at least said first protective package that contains at least the cutting edges of the surgical tool in the shell of a blister pack, such that said first protective package is secured in a fixed position in said shell of said blister pack with at least a portion of the shaft of the surgical tool extending outside of the second package part of the first protective package and protruding into the shell of the blister pack without contacting the inner surfaces of the blister pack; and sealing the blister pack with a sealing film.

2. A package for sterile surgical tools, the package comprising:

an inner protective package that is configured to completely surround the cutting edges of a surgical tool, said inner protective package having inner surfaces that define an interior chamber with the cutting edges of said surgical tool being spaced apart from all of said inner surfaces, said inner protective package having a first package part with a surface that defines an interior chamber into which the cutting edges of the surgical tool protrude with the surgical tool being spaced apart from the surface that defines the interior chamber, said inner protective package also having a second package part that accommodates at least a portion of a shaft of the surgical tool, the second package part including at least one holding element that is configured to secure the shaft of the surgical tool in a fixed position within said second package part with at least a portion of the shaft of the surgical tool extending outside of the second package part of the inner protective package; and an outer blister pack that includes a shell that defines an interior space and that is configured to accommodate and secure the inner protective package in a fixed position within the interior space of the shell of said outer blister pack with the portion of the surgical tool that extends outside of the second package part also extends into the interior space of the shell of the blister pack, and with the portion of the surgical tool that extends outside of the second package also being spaced apart from the surface of the shell of the blister pack, said outer blister pack further including a sealing film that cooperates with said shell of the blister pack to seal said inner protective package within said blister pack.

3. The package according to claim 2, wherein the portion of the surgical tool extending outside of the second package part is spaced apart from the surface of the shell of the blister pack and only the inner protective package contacts the inner surface of the shell of the outer blister pack.

4. A method of packaging sterile surgical tools, the method comprising:

placing at least the cutting edges of a surgical tool in a first protective package that includes a first package part and a second package part, said first package part having internal surfaces that define an interior chamber into which the cutting edges of the surgical tool protrude without contacting said internal surfaces of the first package part, said second package part accommodating at least a portion of a shaft of the surgical tool and including at least one holding element that is configured to secure said shaft of the surgical tool in a fixed position with at least a portion of said shaft of the surgical tool extending outside of the said second package part;

placing at least said first package part in the shell of a blister pack, such that said first package part is secured in a fixed position in said shell of said blister pack with said portion of said shaft of the surgical tool that extends outside of the said second package part protruding into the shell of the blister pack without contacting the inner surfaces of the blister pack; and sealing the blister pack with a sealing film.

5. A package for sterile surgical tools, the package comprising:

an inner protective package that is configured to contain at least the cutting edges of a surgical tool, said inner protective package having a first package part and a second package part, said first package part having a surface that defines an interior chamber into which the cutting edges of the surgical tool protrude with the surgical tool being spaced apart from the surface that defines the interior chamber; and said second package part accommodating at least a portion of a shaft of the surgical tool with at least a portion of the shaft of the surgical tool extending outside of the second package part, said second package part including at least one holding element that is configured to secure the shaft of the surgical tool in a fixed position within said second package part; and an outer blister pack that includes a shell that defines an interior space and that is configured to accommodate and secure the inner protective package in a fixed position within the interior space of the shell of said outer blister pack with the portion of the surgical tool that extends outside of the second package part also extending into the interior space of the shell of the blister pack and spaced apart from the surface of the shell of the blister pack, said outer blister pack further including a sealing film that cooperates with said shell to seal said inner protective package within said blister pack.

6. The package according to claim 5, wherein the portion of the surgical tool extending outside of the second package part is spaced apart from the surface of the shell of the blister pack and only the inner protective package contacts the inner surface of the shell of the outer blister pack.

* * * * *